(12) United States Patent
Melchiorri et al.

(10) Patent No.: US 9,282,948 B2
(45) Date of Patent: Mar. 15, 2016

(54) TOTAL CORE BIOPSY DEVICE AND METHOD OF USE

(75) Inventors: Anthony J. Melchiorri, Normal, IL (US); Allen E. Hacker, Bloomington, IN (US); Casey L. Brown, Bedford, IN (US); Chris Ferree, Bloomington, IN (US); Danielle N. Joaquin, Tinley Park, IL (US); Torsten Schreiber, Indianapolis, IN (US); Ryan Krieger, Ann Arbor, MI (US); Vincent Mangus, Ellettsville, IN (US); John R. Brumleve, Indianapolis, IN (US); Chase Wooley, Floyds Knobs, IN (US); Brent Hillard, Elizabethtown, KY (US); Bill Prosise, Bloomington, IN (US); Gregg Arthur, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 505 days.

(21) Appl. No.: 13/398,315

(22) Filed: Feb. 16, 2012

(65) Prior Publication Data
US 2012/0265097 A1    Oct. 18, 2012

Related U.S. Application Data

(60) Provisional application No. 61/445,294, filed on Feb. 22, 2011.

(51) Int. Cl.
*A61B 5/00* (2006.01)
*A61B 10/02* (2006.01)

(52) U.S. Cl.
CPC ..... *A61B 10/0266* (2013.01); *A61B 2010/0208* (2013.01)

(58) Field of Classification Search
CPC ............ A61B 10/0266; A61B 2010/0208; A61B 2017/07278
USPC .................................. 600/564–567
See application file for complete search history.

(56) References Cited

U.S. PATENT DOCUMENTS

| 2,919,692 | A | * | 1/1960 | Ackermann | 600/567 |
| 3,513,830 | A | * | 5/1970 | Kalayjian | 600/572 |
| 4,055,167 | A | | 10/1977 | Bernstein | |
| 4,457,313 | A | * | 7/1984 | Alter | 600/572 |
| 4,627,444 | A | | 12/1986 | Brooker | |
| 4,702,260 | A | | 10/1987 | Wang | |

(Continued)

FOREIGN PATENT DOCUMENTS

CN    2449657 Y    9/2001

OTHER PUBLICATIONS

Chhieng, David C. et al., "Fine-Needle Aspiration Cytology of Hodgkin Disease," Cancer Cytopathology, 2001, American Cancer Society, pp. 52-59.

(Continued)

*Primary Examiner* — Max Hindenburg
(74) *Attorney, Agent, or Firm* — Brinks Gilson & Lione

(57) ABSTRACT

Total core biopsy devices and methods of use are provided for taking a total core biopsy sample and a means for using the devices that provide for an adequate sample size and quality while being light-weight, easy to use, small, inexpensive, and permitting one-handed operation and beveled edges to reduce trauma to the surrounding tissue and organs from which a total core biopsy sample may be taken.

15 Claims, 7 Drawing Sheets

(56) References Cited

U.S. PATENT DOCUMENTS

| | | | | |
|---|---|---|---|---|
| 4,785,826 A | * | 11/1988 | Ward | 600/567 |
| 4,791,937 A | | 12/1988 | Wang | |
| 4,900,300 A | | 2/1990 | Lee | |
| 4,903,709 A | | 2/1990 | Skinner | |
| 4,940,061 A | * | 7/1990 | Terwilliger et al. | 600/567 |
| 4,953,558 A | * | 9/1990 | Akerfeldt | 600/564 |
| 4,989,614 A | | 2/1991 | Dejter, Jr. et al. | |
| 4,991,592 A | | 2/1991 | Christ | |
| 5,106,364 A | | 4/1992 | Hayafuji et al. | |
| 5,267,572 A | * | 12/1993 | Bucalo | 600/567 |
| 5,320,110 A | | 6/1994 | Wang | |
| 5,449,001 A | | 9/1995 | Terwilliger | |
| 5,458,112 A | | 10/1995 | Weaver | |
| 5,470,308 A | | 11/1995 | Edwards et al. | |
| 5,505,210 A | * | 4/1996 | Clement | 600/566 |
| 5,573,008 A | * | 11/1996 | Robinson et al. | 600/567 |
| 5,615,690 A | * | 4/1997 | Giurtino et al. | 600/567 |
| 5,807,304 A | | 9/1998 | Cockburn | |
| 5,817,033 A | | 10/1998 | DeSantis et al. | |
| 5,865,765 A | | 2/1999 | Mohajer | |
| 5,885,226 A | * | 3/1999 | Rubinstein et al. | 600/564 |
| 5,910,121 A | * | 6/1999 | Paolo et al. | 600/562 |
| 5,971,939 A | | 10/1999 | DeSantis et al. | |
| 6,176,834 B1 | * | 1/2001 | Chu et al. | 600/567 |
| 6,709,408 B2 | | 3/2004 | Fisher | |
| 6,855,107 B2 | * | 2/2005 | Avni et al. | 600/114 |
| 7,347,829 B2 | * | 3/2008 | Mark et al. | 600/567 |
| 8,162,850 B2 | * | 4/2012 | Parihar et al. | 600/565 |
| 8,187,203 B2 | * | 5/2012 | McClellan | 600/567 |
| 8,337,414 B2 | * | 12/2012 | Vetter et al. | 600/567 |
| 8,475,393 B1 | * | 7/2013 | Hameed et al. | 600/564 |
| 8,690,793 B2 | * | 4/2014 | Ranpura et al. | 600/562 |
| 2009/0118641 A1 | | 5/2009 | Van Dam et al. | |

OTHER PUBLICATIONS

Davenport, R.D., "Rapid on-site evaluation of transbronchial aspirates," Chest, 1990, vol. 98, pp. 59-61.

Diette, Gregory B., "Utility of On-Site Cytopathology Assessment for Bronchoscopic Evaluation of Lung Masses and Adenopathy," Chest, 2000, vol. 117, pp. 1186-1190.

Gittlen, S.D., "A new versatile transbronchial cytology needle for the staging and diagnosis of bronchogenic carcinoma," Chest, 1988, vol. 94, pp. 561-565.

Kaffes, Arthur J., "Fine Needle Aspiration At Endoscopic Ultrasound With a Novel Olympus Side-Port Needle: A Pilot Experience," Gastrointestinal Endoscopy, Abstract T1492, 2010, vol. 71, No. 5, p. 291.

Mayall, Frederick et al., "Improved FNA cytology results with a near patient diagnosis service for non-breast lesions," J. Clin. Pathol., 1998, vol. 51, pp. 541-544.

Mazzone MD, Peter et al., "Bronchoscopy and Needle Biopsy Techniques for Diagnosis and Staging of Lung Cancer," Clinics in Chest Medicine, vol. 23, No. 1, Mar. 2002, pp. 137-158.

McLoud MD, Theresa C., "Should Cutting Needles Replace Needle Aspiration of Lung Lesions?", Radiology, Jun. 1998, pp. 569-570.

Olympus KeyMed, Diagnosis (Needle Aspiration), keymed.co.uk/index.cfm/page/.../615, 2010, 2 pages.

Olympus EndoTherpay, SmoothShot, Expanded Line of Transbronchial Aspiration Needles Provides Comprehensive Scope Compatibility, Exceptional Puncture Performance, and Improved Operability, date unknown, 3 pages.

Shure, D., "Transbronchial biopsy and needle aspiration," Chest, 1989, vol. 95, pp. 1130-1138.

Trumm, C.G. et al., "Biopsy," Ch. 9, date unknown, pp. 94-95.

Wang, K.P., "Flexible transbronchial needle aspiration biopsy for histologic specimens," Chest, 1985, vol. 88, pp. 860-863.

Wang, Ko Pen, "Biopsy Sampling Techniques," Chest, 1989, vol. 95, pp. 484-485.

Wang, K.P. et al., "Needle brush in the diagnosis of lung mass or nodule through flexible bronchoscopy," Chest, 1991, vol. 100, pp. 1148-1150.

Weisbrod, Gordon L. et al., "Preliminary Experience with a Dual Cutting Edge Needle in Thoracic Percutaneous Fine-Needle Aspiration Biopsy," Radiology, Apr. 1987, pp. 75-78.

Yang, Grace, C.H. et al., "Ultrasound-Guided Fine-Needle Aspiration of the Thyroid Assessed by Ultrafast Papanicolaou Stain: Data from 1135 Biopsies with a Two to Six Year Follow-Up," Thyroid, vol. 11, No. 6, 2001, pp. 581-589.

\* cited by examiner

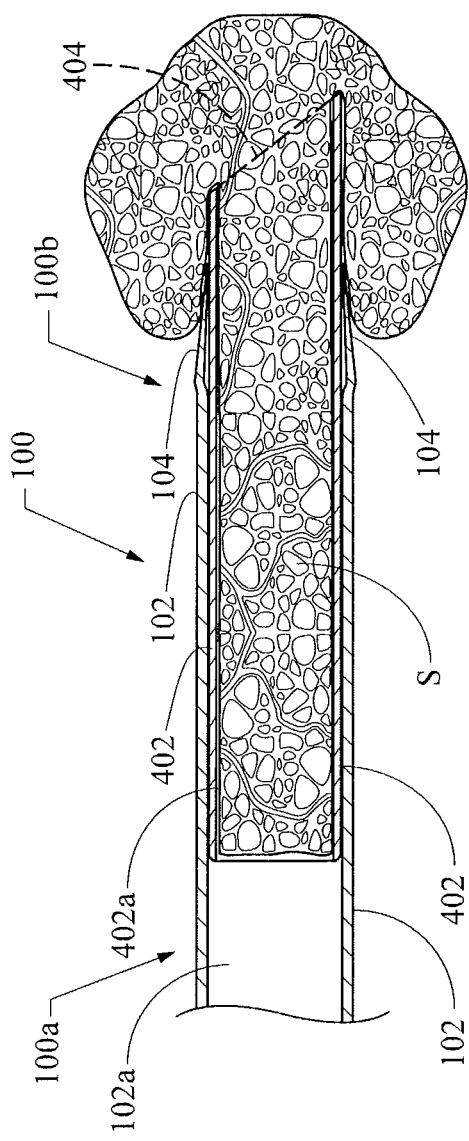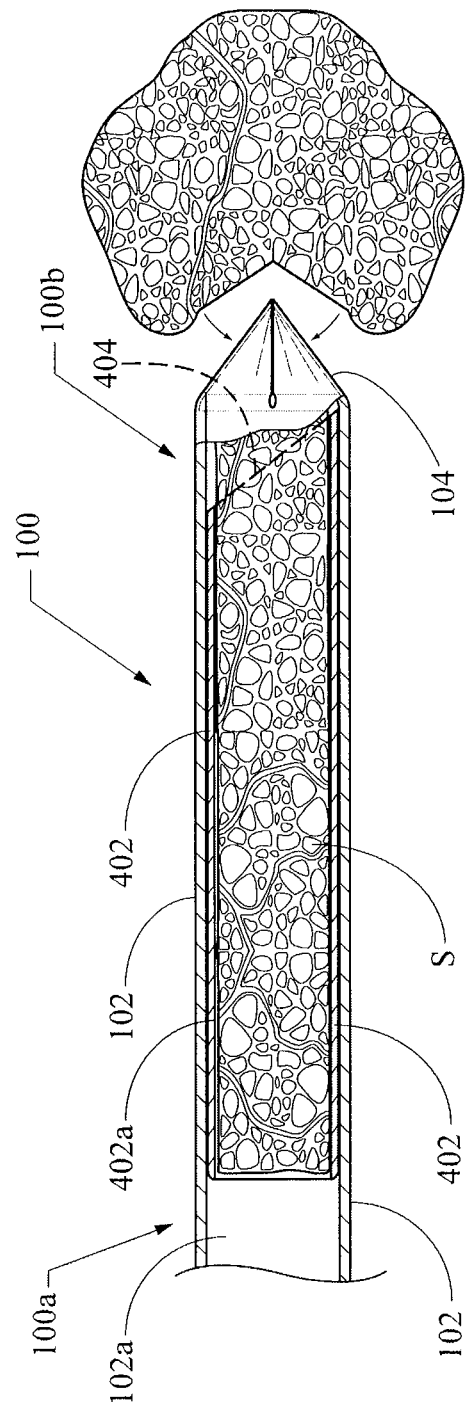

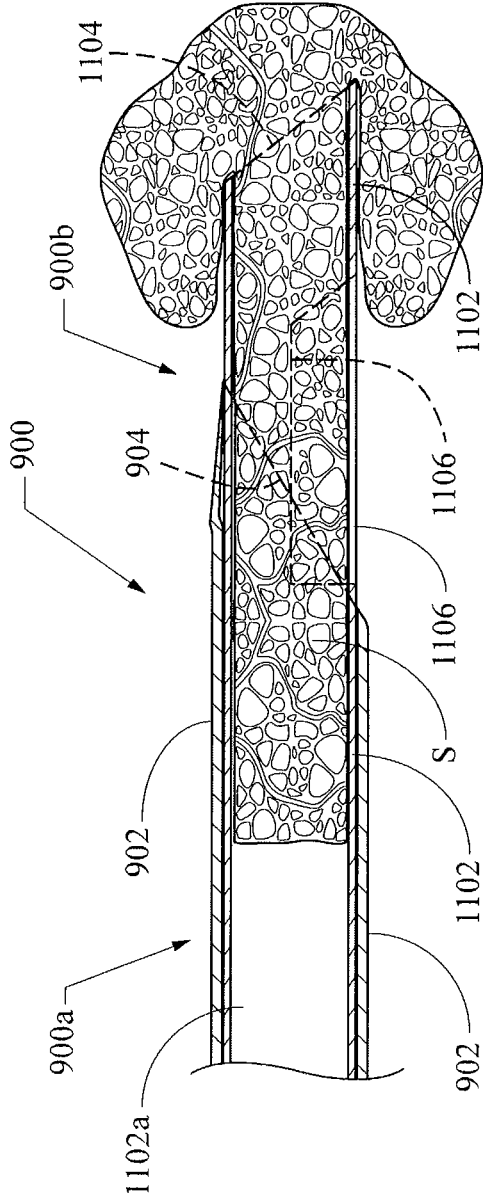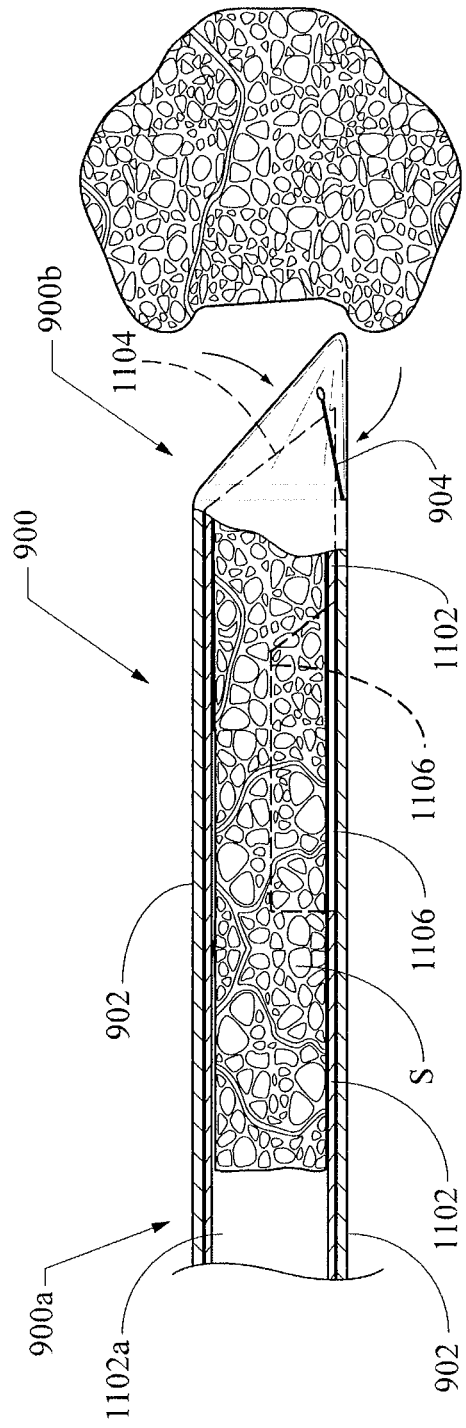

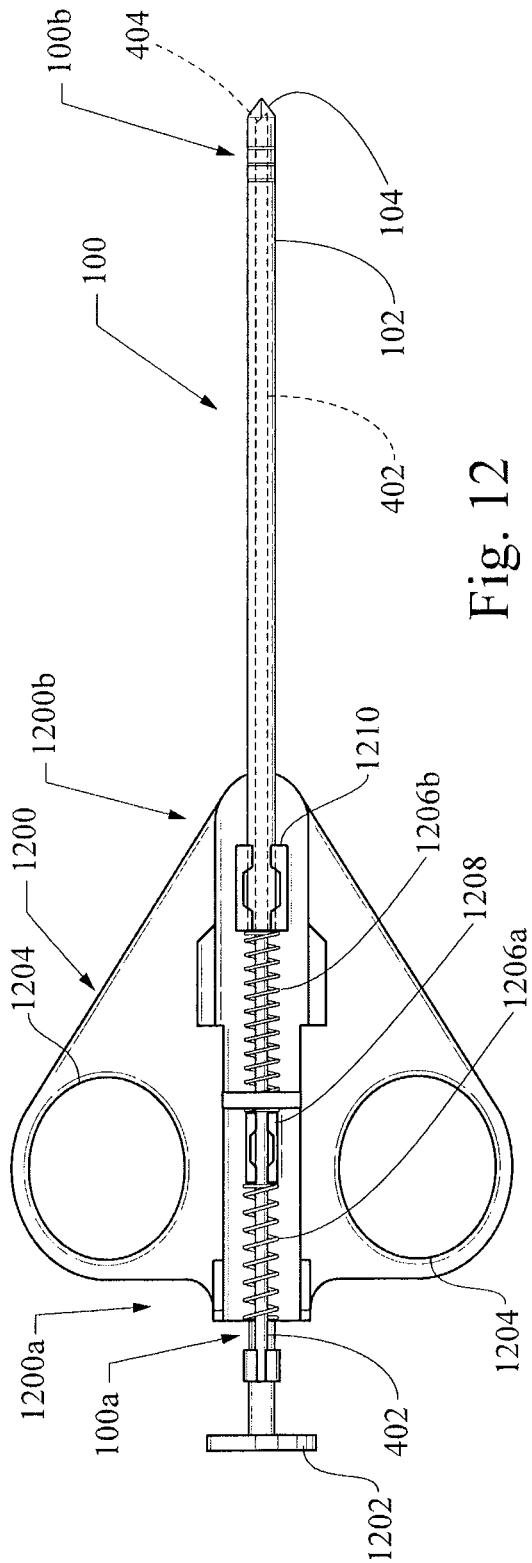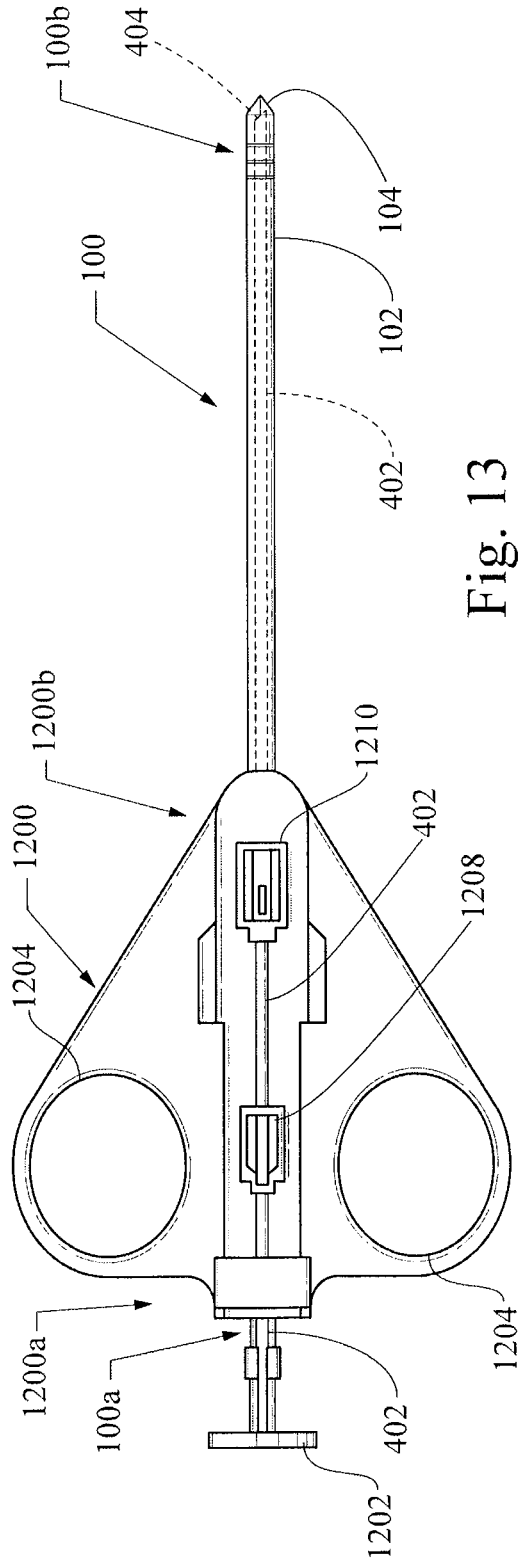

TOTAL CORE BIOPSY DEVICE AND METHOD OF USE

CROSS REFERENCE TO RELATED APPLICATION

This application claims the benefit of priority from U.S. Provisional Application No. 61/445,294, filed Feb. 22, 2011, which is hereby incorporated by reference in its entirety.

TECHNICAL FIELD

The present invention relates to medical devices and more specifically, biopsy devices.

BACKGROUND

Biopsies are important medical tests used to collect cells or tissue for examination so as to determine the presence, extent, or likelihood of disease, trauma, ailment, or for other diagnostic or therapeutic applications. Biopsies are generally painful procedures, and current devices used to collect samples suffer from many shortcomings such as being bulky or not being able to collect a complete core sample. Biopsy collection devices also cause unnecessary trauma to the surrounding tissue by ripping or tearing the sample from its original dwelling.

BRIEF SUMMARY

In a first aspect, a biopsy device is provided having an outer cannula having a proximal portion, a distal portion, and a lumen extending between the proximal portion and the distal portion, wherein the distal portion includes a cutting edge configured for cutting a biopsy sample; the device further includes an inner cannula having a proximal portion, a distal portion, and a lumen extending between the proximal portion and the distal portion configured for accepting a core biopsy sample, wherein the distal portion of the inner cannula includes a cutting edge configured for cutting a biopsy sample, wherein the inner cannula is partially disposed within the lumen of the outer cannula, and wherein the inner cannula is configured for axial movement out from the cutting edge of the outer cannula; wherein the cutting edge of the outer cannula is biased to close the lumen of the outer cannula and configured to open the lumen of the outer cannula when a force is applied to an inside surface of the cutting edge of the outer cannula by the inner cannula.

In a second aspect, a method for taking a total core biopsy is provided comprising the steps of providing a total core biopsy device including: an outer cannula having a proximal portion, a distal portion, and a lumen extending between the proximal portion and the distal portion, wherein the distal portion includes a cutting edge configured for cutting a biopsy sample; an inner cannula having a proximal portion, a distal portion, and a lumen extending between the proximal portion and the distal portion configured for accepting a core biopsy sample, wherein the distal portion of the inner cannula includes a cutting edge configured for cutting a biopsy sample, wherein the inner cannula is partially disposed within the lumen of the outer cannula, and wherein the inner cannula is configured for axial movement out from the cutting edge of the outer cannula; wherein the cutting edge of the outer cannula is biased to close the lumen of the outer cannula and configured to open the lumen of the outer cannula when a force is applied to an inside surface of the cutting edge of the outer cannula by the inner cannula; configuring the total core biopsy device wherein the cutting edge of the inner cannula is disposed within the lumen of the outer cannula and wherein the cutting edge of the outer cannula is closed; positioning the total core biopsy device over a biopsy site; directing the inner cannula in a distal direction wherein the cutting edge of the outer cannula opens and the inner cannula cuts a portion of a biopsy sample and is gathered within the lumen of the inner cannula; and directing the outer cannula in a distal direction over the inner cannula wherein the cutting edge of the outer cannula closes and severs the biopsy sample.

In a third aspect, a handle for use with total core biopsy device is provided having a distal portion and a proximal portion, wherein the distal portion is configured for receiving a total core biopsy device, and wherein the proximal portion of the handle is configured for axially advancing and withdrawing an inner cannula of the total core biopsy device, wherein the inner cannula advances out from an outer cannula of the total core biopsy device so as to open a biased closed cutting edge of the outer cannula, and wherein the inner cannula withdrawals from the outer cannula so as to close a biased close cutting edge of the outer cannula.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims.

FIG. 5 illustrates a cross-sectional side view of an exemplary total core biopsy device in use;

FIG. 6 illustrates a partial cross-sectional side view of an exemplary total core biopsy device in use;

FIG. 10 illustrates a cross-sectional side view of an exemplary total core biopsy device in use;

FIG. 11 illustrates a partial cross-sectional side view of an exemplary total core biopsy device in use;

FIG. 12 illustrates a top view of an exemplary handle for use with a total core biopsy device;

FIG. 13 illustrates a bottom view of an exemplary handle for use with a total core biopsy device;

DETAILED DESCRIPTION OF PRESENTLY PREFERRED EMBODIMENTS

Figure 1:
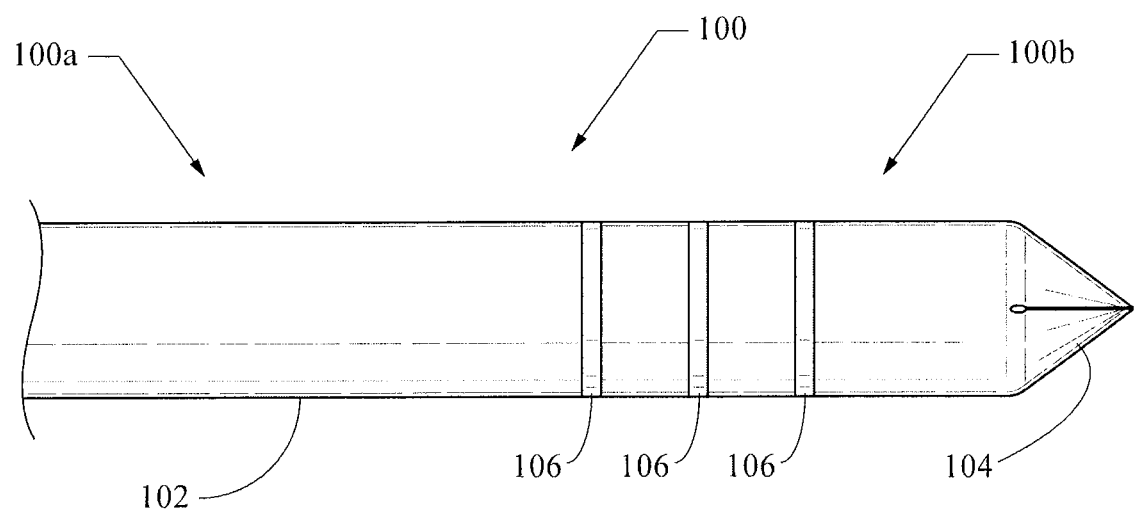
FIG. 1 illustrates a side view of an exemplary total core biopsy device for collecting a total core biopsy sample.

The exemplary embodiments illustrated herein provide exemplary apparatuses and methods for collecting a total core biopsy sample. The present invention is not limited to those embodiments described herein, but rather, the disclosure includes all equivalents including those of different shapes and sizes. The devices can be used in any field benefiting from a biopsy sample.

A more detailed description of the embodiments will now be given with reference to FIGS. 1-15. Throughout the disclosure, like reference numerals and letters refer to like elements. The present disclosure is not limited to the embodiments illustrated; to the contrary, the present disclosure specifically contemplates other embodiments not illustrated but intended to be included in the claims.

It has been discovered that a double cannula, light-weight, easy to use, small, inexpensive device permitting one-handed operation and a beveled edge can be created to reduce trauma to the surrounding tissue and organs and take a total core sample such that the problem of inadequate sample size is solved.

FIG. 1 illustrates a side view of an exemplary total core biopsy device for collecting a total core biopsy sample. Device 100 has proximal portion 100a, distal portion 100b, outer cannula 102, and optional markers 106. Although three markers 106 are illustrated more or less markers 106 can be used, including none. Optional markers 106 are made from Platinum-Iridium alloy or any other echogenic material, including but not limited to, gold and tungsten. An echogenic material includes surface irregularities that reflect ultrasonic waves and thus, allows the material to be seen with ultrasonic imaging devices. Echogenic techniques are described in U.S. Pat. No. 5,081,997 and U.S. Pat. No. 5,289,831, and are hereby incorporated by reference in their entirety. It is contemplated that markers 106 can be manufactured in whole or in part from other materials, including but not limited to, stainless steel or other suitable medical-grade materials, including but not limited to, radiopaque materials, such that the material provides for visualization outside the patient using a visualization device, including but not limited to, fluoroscopy, x-ray, and magnetic resonance imaging (MRI).

As illustrated here, markers 106 are etched with a pattern which provides for visualization using ultrasound (or other visualization technique) such that the user knows the depth of outer cannula within a body. Body is not limited to a human body; indeed others are contemplated, including but not limited to, animals. User is not limited to a human being; indeed anything capable of using the device is contemplated, including but not limited to, a machine.

Figure 2:
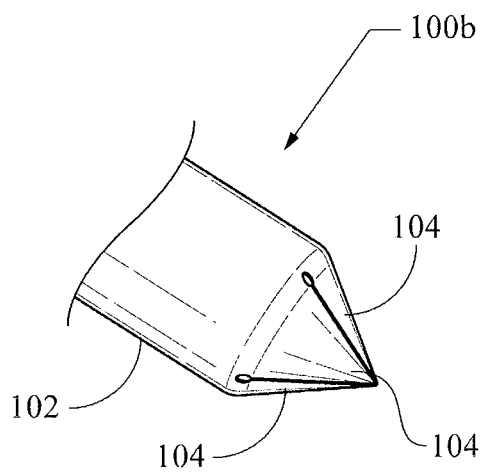
FIG. 2 illustrates a perspective view of an exemplary total core biopsy device for collecting a total core biopsy sample wherein the outer cutting edge is illustrated in a closed position.

Outer cannula 102 has cutting edge 104. Cutting edge 104 of outer cannula 102 (and the cutting edge of other outer cannulas contemplated) is made from nickel titanium (nitinol) or any other material that provides for biasing a material into a certain position wherein the material attempts to reassume that biased position when put into a position different from the biased position. Cutting edge 104 is sharpened to efficiently cut through tissue, muscle, or other material from which a biopsy sample is to be taken. Cutting edge 104 is heat-set in a closed position such that cutting edge 104 is biased to assume a closed position as illustrated in FIGS. 1 and 2. The remainder of outer cannula 102 (and other outer cannulas contemplated) is also made from nitinol or any other material having properties similar to nitinol such that the material is configurable into a biased position, and when out from that position is biased to resume the initial biased position, including but not limited to echogenic and other materials that may or may not provide for visualization using a visualization device, including but not limited to fluoroscopy, x-ray, ultrasound, or MRI.

It is contemplated that outer cannula can be configured to have a variety of gauges and lengths depending upon the needs of the patient and the area from which the biopsy sample is to be taken.

As illustrated in FIG. 1, cutting edge 104 has a three-leaf/petal design and sharpened edges, such as being razor sharp, to provide for an efficient cutting edge for cutting tissue, muscle, or other material from a body. Although illustrated as three-leafs, other cutting edges are contemplated such that cutting edge is biased in a closed position and is able to be opened from a force applied to an interior surface of the cutting edge.

Figure 3:
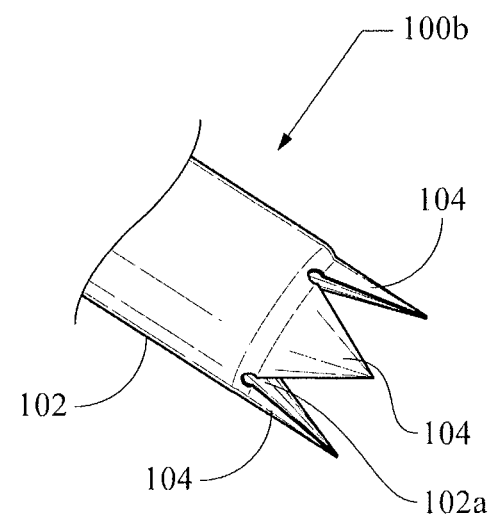
FIG. 3 illustrates a perspective view of an exemplary total core biopsy device for collecting a total core biopsy sample wherein the outer cutting edge is illustrated an open position.

FIG. 2 illustrates a perspective view of an exemplary total core biopsy device 100 for collecting a total core biopsy sample wherein cutting edge 104 of outer cannula 102 is illustrated in a closed position. FIG. 3 illustrates a perspective view of an exemplary total core biopsy device 100 for collecting a total core biopsy sample wherein cutting edge 104 of outer cannula 102 is illustrated in an open position exposing lumen 102a of outer cannula 102.

Figure 4:
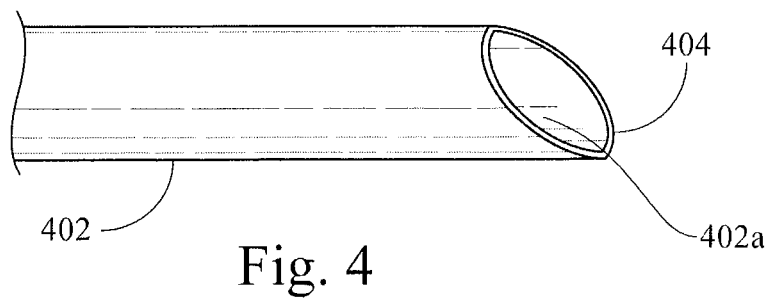
FIG. 4 illustrates a perspective view of an exemplary inner cannula.

FIG. 4 illustrates a perspective view of an exemplary inner cannula 402 having lumen 402a extending there through. Cutting edge 404 is optionally beveled, and it is sharpened, such as being sharpened to a razor point, to provide for an efficient cutting edge for cutting tissue, muscle, or other material from a body. Inner cannula 402 (and other inner cannulas contemplated) is made from stainless steel. However, it is contemplated that inner cannula 402 (and other inner cannulas contemplated) can be made from other materials, including but not limited to, being manufactured in whole or in part from plastic or other suitable medical-grade materials, including but not limited to, echogenic and other materials that may or may not provide for visualization using a visualization device, including but not limited to fluoroscopy, x-ray, ultrasound, or MRI. Additionally, inner cannula 402 (and other inner cannulas contemplated) can also include any number of markers, such as those illustrated in FIG. 1, including none. It is contemplated that inner cannula can be configured to have a variety of gauges and lengths depending upon the needs of the patient and the area from which the biopsy sample is to be taken.

Inner cannula 402 is disposed within outer cannula 102 such that inner cannula 402 optionally fits snugly within outer cannula 102, but with enough space disposed between inner cannula 402 and outer cannula 102 such that inner cannula 402 can be moved axially, both proximally 100a and distally 100b relative to outer cannula 102.

FIG. 5 illustrates a cross-sectional side view of an exemplary total core biopsy device 100 in use. Device 100 is directed to the area from where the biopsy sample is to be taken wherein cutting edge 404 of inner cannula 402 is disposed within outer cannula 102 such that cutting edge 104 of outer cannula 102 is closed, as illustrated in FIG. 1. Inner cannula 402 is then advanced in a distal direction 100b out from outer cannula 102 such that cutting edge 104 of outer cannula 102 opens from the force exerted by inner cannula 402 engaging the interior surface of cutting edge 104 of outer cannula 102. Cutting edge 404 of inner cannula 402 subsequently cuts tissue sample S as it pierces it, severing it from its original site, and collecting it in lumen 402a of inner cannula 402.

FIG. 6 illustrates a partial cross-sectional side view of an exemplary total core biopsy device 100 in use. After inner cannula 402 has cut biopsy sample S (as shown in FIG. 5), outer cannula 102 is drawn over inner cannula 402, such that cutting edge 104 of outer cannula 102 moves to its biased-closed position to thereby cut the remainder of sample S from its original location. Thus, a total core sample has been collected within lumen 402a of inner cannula 402.

Figure 7:
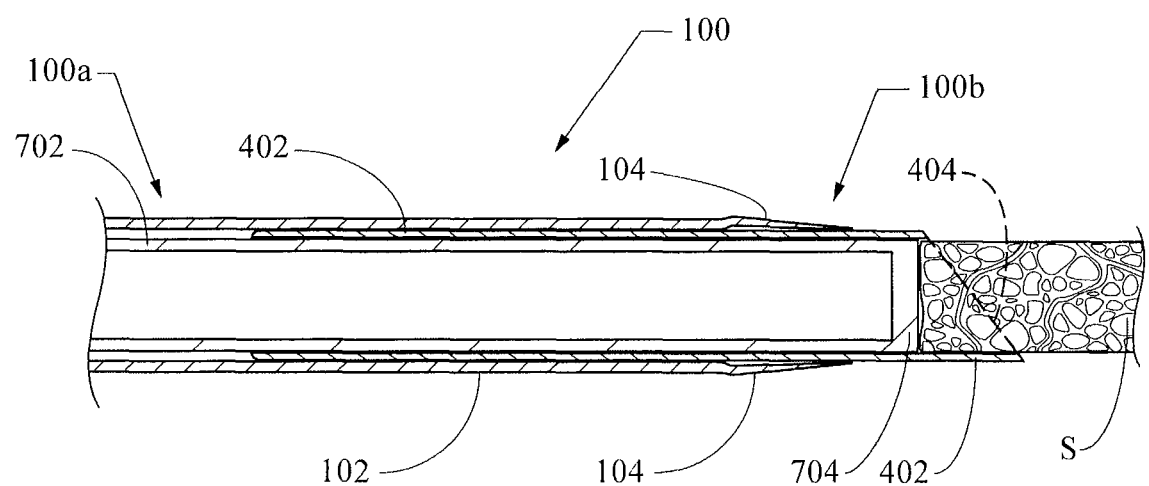
FIG. 7 illustrates a cross-sectional side view of an exemplary total core biopsy device for collecting a total core biopsy sample having an optional stylet in use.

FIG. 7 illustrates a cross-sectional side view of an exemplary total core biopsy device 100 for collecting a total core biopsy sample having optional stylet 702. Stylet 702 is closed at its distal-most end 704 such that it provides a pushing surface to aid the ejection of sample S subsequent to its collection (as shown in FIG. 6). As illustrated in FIG. 7, sample S is being ejected from device 100 by advancing stylet 702 in a distal direction 100b.

Figure 8:
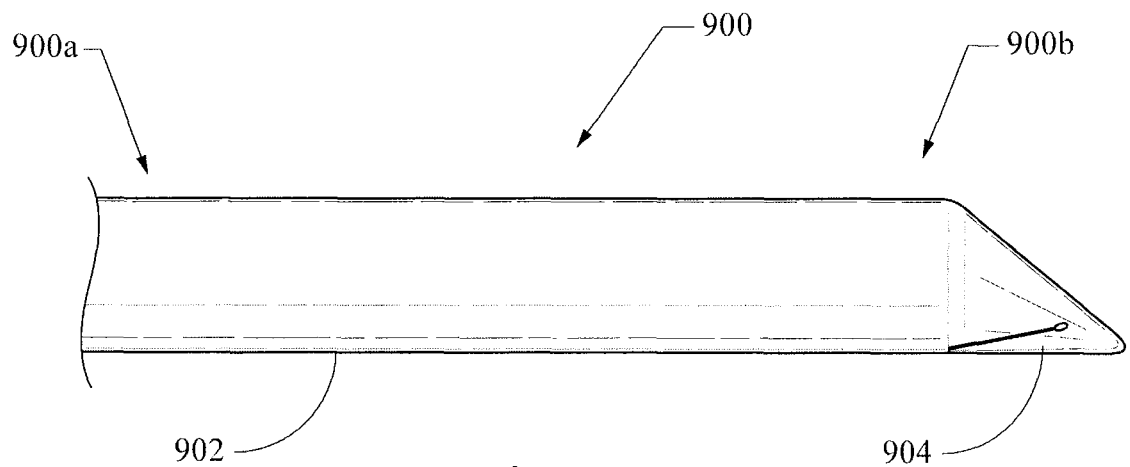
FIG. 8 illustrates a side view of an alternate exemplary total core biopsy device for collecting a total core biopsy sample.
Figure 9:
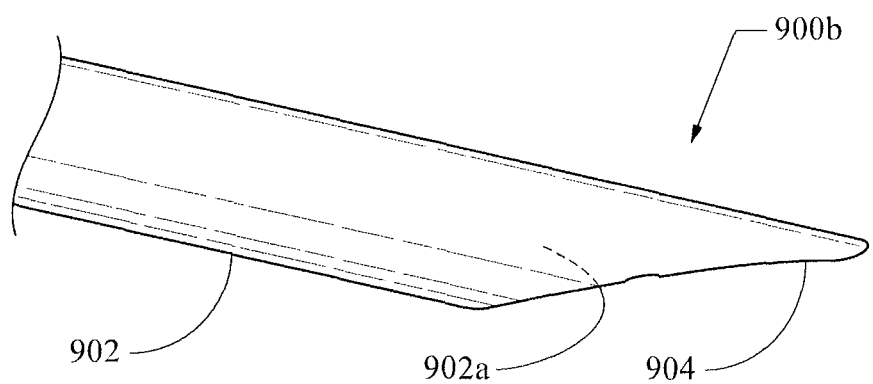
FIG. 9 illustrates a side view of an exemplary outer cannula in an open position.

FIGS. 8 and 9 illustrate an alternate exemplary total core biopsy device 900 for collecting a total core biopsy sample, wherein device 900 has proximal portion 900a and distal portion 900b. FIG. 8 illustrates a side view of device 900 and FIG. 9 illustrates a perspective view of device 900. The total core biopsy device 900 includes an exemplary outer cannula 902 including a lumen 902a extending there through. As illustrated in FIG. 8, device 900 has outer cannula 902 with cutting edge 904 that includes one flap that is heat-set at a closed position such that cutting edge 904 is biased to assume a closed position. FIG. 9 illustrates cutting edge 904 of outer cannula 902 in an open position.

FIG. 10 illustrates a cross-sectional side view of an exemplary total core biopsy device 900 in use. More particularly, device 900 is directed to the area from where the biopsy sample is to be taken wherein cutting edge 1104 of inner cannula 1102 is disposed within outer cannula 902, such that cutting edge 904 of outer cannula 902 is closed, as illustrated in FIG. 8. Inner cannula 1102 is then advanced in a distal direction 900b out from outer cannula 902 such that cutting edge 904 of outer cannula 902 opens from the force exerted by inner cannula 1102 engaging cutting edge 904 of outer cannula 902. Cutting edge 1104 of inner cannula 1102 cuts tissue sample S as it pierces it, severing it from its original site, and collecting it in lumen 1102a of inner cannula 1102.

FIG. 11 illustrates a partial cross-sectional side view of an exemplary total core biopsy device 900 in use. After inner cannula 1102 has cut biopsy sample S (as shown in FIG. 10), outer cannula 902 is drawn over inner cannula 1102, such that cutting edge 904 of outer cannula 902 moves to its biased-closed position cutting the remainder of sample S from its original location. Sample S can be ejected from optional notch 1106 and distal portion 900b of inner cannula 1102. An optional stylet can also be used, as illustrated in FIG. 7.

Figure 14:
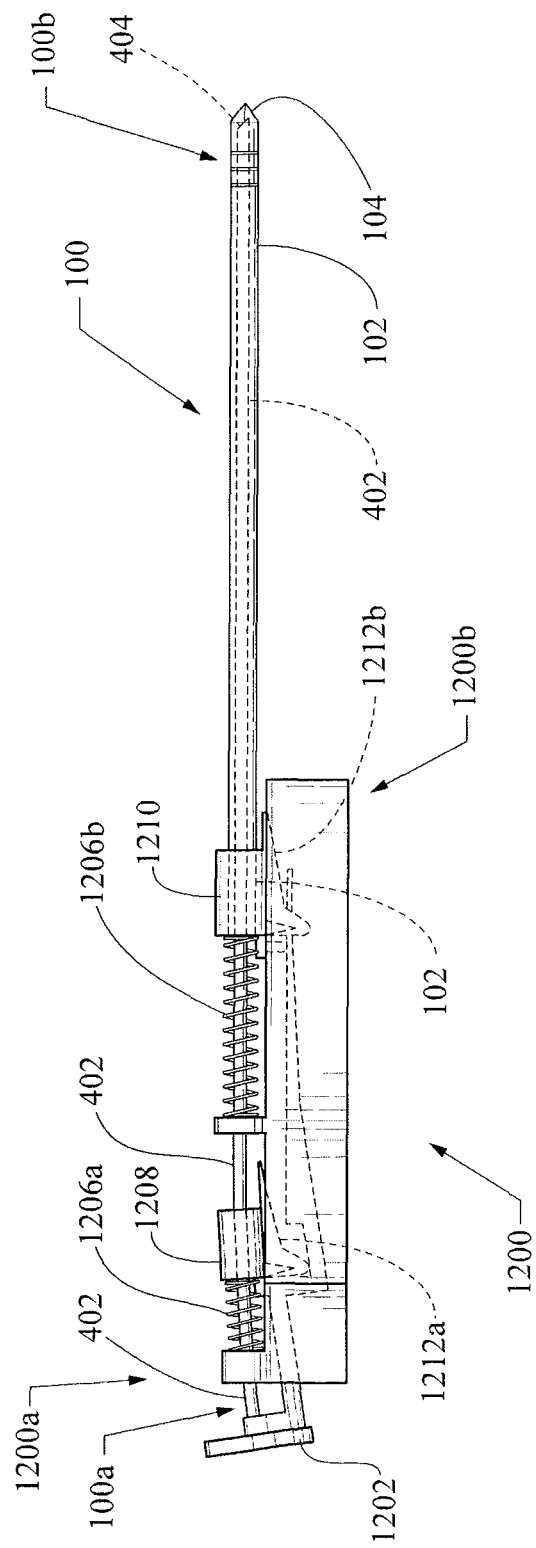
FIG. 14 illustrates a partial cross-sectional side view of an exemplary handle for use with a total core biopsy device.

FIG. 12 illustrates a top view of an exemplary handle 1200 for use with a total biopsy device for collecting a total core biopsy sample, such as those illustrated herein; FIG. 13 illustrates a bottom view of the same; and FIG. 14 illustrates a side view of the same. As illustrated in FIGS. 12-14, handle 1200 has proximal portion 1200a, distal portion 1200b, and finger loops 1204 to aid in holding handle 1200. Other means for holding the device are contemplated.

Plunger 1202 is connected to proximal portion 100a of inner cannula 402, which is slidingly engaged with inner cannula sled 1208. Outer cannula 102 is slidingly engaged with outer cannula sled 1210. When plunger 1202 is pulled in a proximal direction 1200a, outer cannula sled 1210 is first cocked followed by inner cannula sled 1208 causing springs 1206b, 1206a to compress, respectively, such that cutting edge 404 of inner cannula 402 is within outer cannula 102 and cutting edge 104 of outer cannula 102 is closed such that biopsy device 100 can be directed to a site for taking a biopsy sample. Once at the site for taking a biopsy, plunger 1202 is moved distally 1200b, inner cannula sled 1208 is fired causing spring 1206a to decompress, releasing inner cannula rocking mechanism 1212a (illustrated in FIG. 14), and moving inner cannula 402 axially in a distal direction 100b causing cutting edge 404 of inner cannula 402 to cut the sample, followed by the release of outer cannula sled 1210, causing spring 1206b to decompress, releasing outer cannula rocking mechanism 1212b (illustrated in FIG. 14), and moving outer cannula 102 axially in a distal direction 100b causing cutting edge 104 of outer cannula 102 to close over distal portion of inner cannula 402 and cut the remaining tissue core sample.

An optional stylet can be pushed distally 100b through plunger 1202 into inner cannula 402 to help eject the sample, or the stylet can optionally be included as a component part of handle 1200 such that when plunger 1202 is pulled in a proximal direction 1200a for a second time, stylet pushes the sample out from inner cannula 402.

Figure 15:
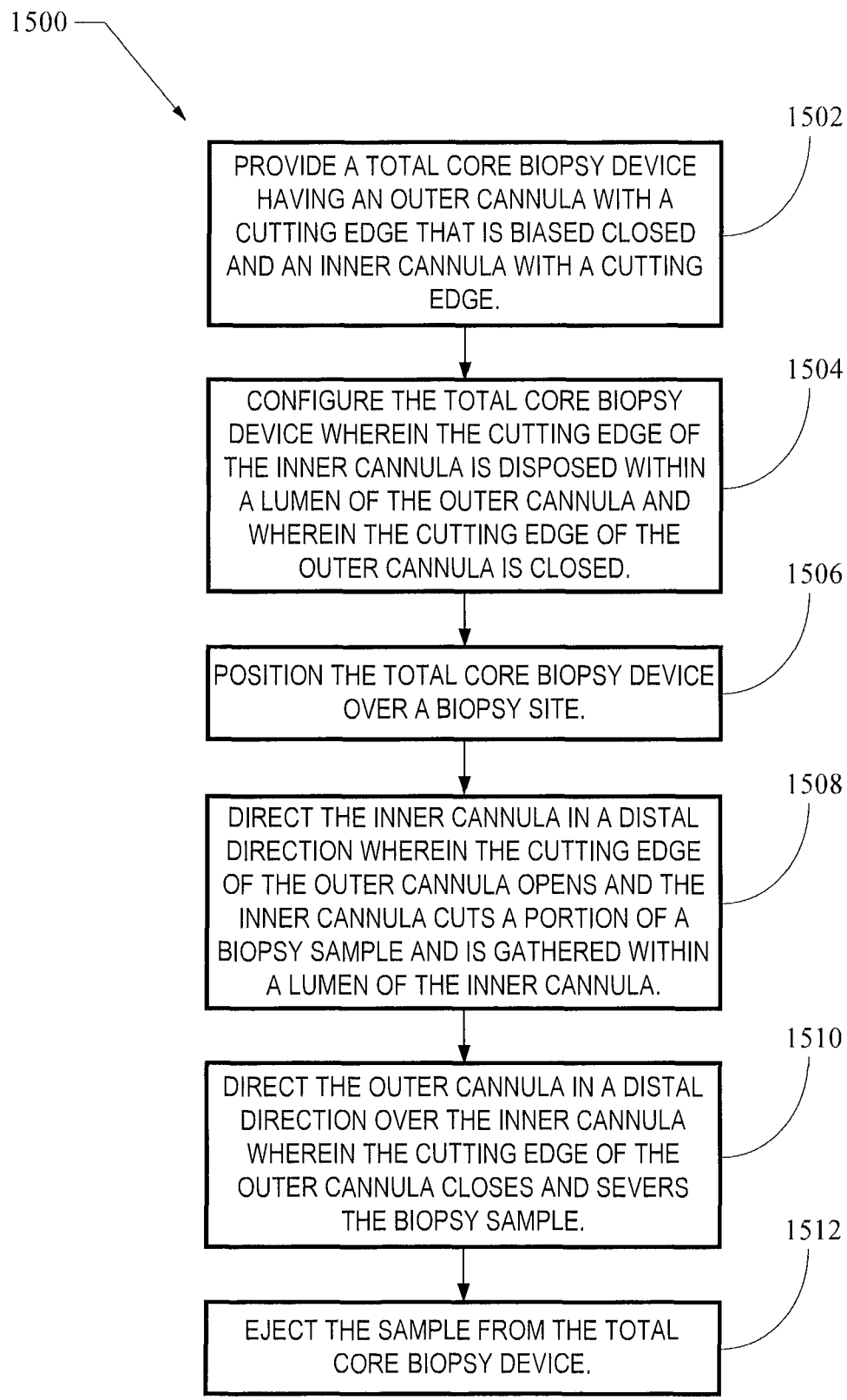
FIG. 15 illustrates a method for taking a total core biopsy sample.

FIG. 15 illustrates a method for taking a total core biopsy sample. Provide a total core biopsy device having an outer cannula with a cutting edge that is biased-closed and an inner cannula with a cutting edge at block 1502. Configure the total core biopsy device wherein the cutting edge of the inner cannula is disposed within a lumen of the outer cannula and wherein the cutting edge of the outer cannula is closed at block 1504. Position the total core biopsy device over a biopsy site at block 1506. Direct the inner cannula in a distal direction wherein the cutting edge of the outer cannula opens and the inner cannula cuts a portion of a biopsy sample and is gathered within a lumen of the inner cannula at block 1508. Direct the outer cannula in a distal direction over the inner cannula wherein the cutting edge of the outer cannula closes and severs the biopsy sample at block 1510. Eject the sample from the total core biopsy device at block 1512.

From the foregoing, it can be seen that the present disclosure provides total core biopsy devices and methods for taking a total core biopsy sample and a means for using the devices, such as a handle. That which is contemplated solves the problem, for example, of an inadequate sample size and quality while providing for light-weight, easy to use, small, inexpensive devices permitting one-handed operation and beveled edges to reduce trauma to the surrounding tissue and organs from which a total core biopsy sample may be taken.

The invention claimed is:

1. A biopsy device comprising:
   an outer cannula having a proximal portion, a distal portion, and a lumen extending between the proximal portion and the distal portion, wherein the distal portion comprises a movable cutting edge configured for cutting an end portion of a biopsy sample;
   an inner cannula having a proximal portion, a distal portion, and a lumen extending between the proximal portion and the distal portion configured for accepting a core biopsy sample, wherein the distal portion of the inner cannula comprises an angled distal end having a cutting edge configured for cutting a circumferential side portion of the biopsy sample without rotation, wherein the inner cannula is partially disposed within the lumen of the outer cannula, and wherein the inner cannula is configured for axial movement out from and distally beyond the cutting edge of the outer cannula;
   wherein the cutting edge of the inner cannula is beveled; and
   wherein the cutting edge of the outer cannula is biased to close the lumen of the outer cannula and retain the biopsy sample there within, and wherein the cutting edge of the inner cannula is configured to open the lumen of the outer cannula when a force is applied to an inside surface of the cutting edge of the outer cannula by axial distal movement of the inner cannula, and wherein the cutting edge of the outer cannula further comprises a unitary flap, the flap movable between a folded configuration and a unfolded configuration, the lumen of the outer cannula being closed when the flap is in the folded configuration, and the lumen of the outer cannula being open when the flap is in the unfolded configuration.

2. The biopsy device of claim 1, further comprising a stylet having a proximal portion and a distal portion, wherein the distal portion is closed and comprises a constant cross-section, and wherein the stylet is configured for at least partial disposition within the lumen of the inner cannula, and the stylet is further configured for axial movement within the lumen of the inner cannula for ejection of a biopsy sample from the inner cannula.

3. The biopsy device of claim 1, where at least one of the outer cannula or inner cannula further comprises a marker disposed about an outer surface of the outer cannula or the inner cannula, wherein the marker is configured for viewing using a visualization device, the visualization device comprising one of fluoroscopy, x-ray, ultrasound, or magnetic resonance imaging (MRI).

4. The biopsy device of claim 3, wherein at least one of the outer cannula or inner cannula comprises a plurality of markers disposed about an outer surface of the outer cannula or the inner cannula at spaced apart locations.

5. The biopsy device of claim 1, wherein the cutting edge of the outer cannula is nickel titanium (nitinol).

6. The biopsy device of claim 1, wherein the cutting edge of the outer cannula is heat-set to a closed position.

7. The biopsy device of claim 1, wherein the inner cannula further comprises a notch disposed within an outer surface of the inner cannula wherein the notch exposes the lumen of the inner cannula to the outer surface of the inner cannula.

8. The biopsy device of claim 1, wherein the inner cannula comprises stainless steel.

9. The biopsy device of claim 1, wherein the outer cannula comprises nitinol.

10. A method for taking a total core biopsy comprising:
providing a total core biopsy device comprising:
an outer cannula having a proximal portion, a distal portion, and a lumen extending between the proximal portion and the distal portion, wherein the distal portion comprises a movable cutting edge configured for cutting a first portion of a biopsy sample;
an inner cannula having a proximal portion, a distal portion, and a lumen extending between the proximal portion and the distal portion configured for accepting a core biopsy sample, wherein the distal portion of the inner cannula comprises an angled distal end having a beveled cutting edge configured for cutting a circumferential second portion of the biopsy sample upon axial movement of the inner cannula, wherein the inner cannula is partially disposed within the lumen of the outer cannula, and wherein the inner cannula is configured for axial movement out from the cutting edge of the outer cannula;
a stylet having a proximal portion and a distal portion, wherein the distal portion is closed and comprises a constant cross-section, the stylet being configured for at least partial disposition within the lumen of the inner cannula, and further being configured for axial movement within the lumen of the inner cannula for ejection of the biopsy sample from the inner cannula;

wherein the cutting edge of the outer cannula is biased to close the lumen of the outer cannula, and is further configured to open the lumen of the outer cannula when a force is applied by the inner cannula to an inside surface of the cutting edge of the outer cannula;

wherein the cutting edge of the outer cannula further comprises a unitary foldable flap movable between a folded configuration and an unfolded configuration, the lumen of the outer cannula being closed when the flap is in the folded configuration, and the lumen of the outer cannula being open when the flap is in the unfolded configuration;

configuring the total core biopsy device wherein the cutting edge of the inner cannula is disposed within the lumen of the outer cannula and wherein the flap of the cutting edge of the outer cannula is in the folded configuration and the lumen of the outer cannula is closed;

positioning the total core biopsy device over a biopsy site;

directing the inner cannula in a distal direction so as to engage and move the flap of the cutting edge of the outer cannula to the unfolded configuration and open the lumen of the outer cannula, and further directing the inner cannula in the distal direction so as to cut and gather a portion of a biopsy sample within the lumen of the inner cannula;

directing the outer cannula in the distal direction over the inner cannula wherein the flap of the cutting edge of the outer cannula severs the biopsy sample and closes the lumen of the outer cannula; and directing the stylet in a distal direction to eject the biopsy sample from the lumen of the inner cannula.

11. The method of claim 10, wherein the positioning of the total core biopsy device over a biopsy site further comprises visualizing markers disposed about the biopsy device using a visualization device.

12. The method of claim 11, wherein the visualization device is one of fluoroscopy, x-ray, ultrasound, or magnetic resonance imaging (MRI).

13. The method of claim 10, wherein the directing of the inner cannula and directing of the outer cannula further comprises using a handle attached to the total core biopsy device, the handle comprising a first sled attached to the inner cannula and configured to axially move the inner cannula, a second sled attached to the outer cannula and configured to axially move the outer cannula, and a plunger configured for firing the first sled to axially drive the inner cannula out from the outer cannula and into a biopsy site, the plunger being further configured for firing the second sled to axially drive the outer cannula over the inner cannula so as to close the cutting edge of the outer cannula and sever the biopsy sample.

14. The biopsy device of claim 1 further comprising a handle, the handle comprising a first sled attached to the inner cannula and configured to axially move the inner cannula, a second sled attached to the outer cannula and configured to axially move the outer cannula, and a plunger configured for firing the first sled to axially drive the inner cannula out from the outer cannula and into a biopsy site, the plunger being further configured for firing the second sled to axially drive the outer cannula over the inner cannula so as to close the cutting edge of the outer cannula and sever the biopsy sample.

15. The biopsy device of claim 14, wherein the handle is configured for the axial passage of a stylet there through and into the inner cannula.

* * * * *